United States Patent
Bak et al.

(10) Patent No.: US 7,875,781 B2
(45) Date of Patent: Jan. 25, 2011

(54) GUZMANIA HYBRID NAMED 'TINTO'

(75) Inventors: Elly Bak, Rijsenhout (NL); Nicolaas D. M. Steur, Oude Niedorp (NL)

(73) Assignee: Corn. Bak B.V., Assendelft (NL)

( * ) Notice: Subject to any disclaimer, the term of this patent is extended or adjusted under 35 U.S.C. 154(b) by 192 days.

(21) Appl. No.: 12/287,919

(22) Filed: Oct. 15, 2008

(65) Prior Publication Data

US 2010/0095419 A1  Apr. 15, 2010

(51) Int. Cl.
*A01H 1/00* (2006.01)
*A01H 5/00* (2006.01)
*A01H 5/10* (2006.01)

(52) U.S. Cl. .................. 800/323; Plt./371; 800/260
(58) Field of Classification Search .............. None
See application file for complete search history.

(56) References Cited

U.S. PATENT DOCUMENTS

PP12,124 P2 * 10/2001 Bak et al. .................. Plt./371
PP13,576 P3 *  2/2003 Bunnik ...................... Plt./371

* cited by examiner

*Primary Examiner*—David H Kruse
(74) *Attorney, Agent, or Firm*—Foley & Lardner LLP

(57) ABSTRACT

A new and distinct *Guzmania* hybrid named 'TINTO' characterized by solid growth habit; funnel-form rosette plant, measuring about 21 cm in height (above the pot when flowering); numerous, relatively narrow, green color foliage, measuring about 23 cm in length and about 2.0 cm to 3.5 cm in width; superior floral bract production; bracts have a unique wine red color which distinguishes this cultivar from typical *Guzmania*; round, singular inflorescence, measuring about 6 cm in height and about 13 cm in diameter; and long-lasting habit.

5 Claims, 2 Drawing Sheets
(2 of 2 Drawing Sheet(s) Filed in Color)

GUZMANIA HYBRID NAMED 'TINTO'

FIELD OF THE INVENTION

The present invention relates to a new, distinct and stable hybrid of *Guzmania* hybrid, hereinafter referred to as 'TINTO'. The present invention relates to seeds which are the *Guzmania* hybrid 'TINTO', as well as, plants and plant parts produced by these seeds which have all of the morphological and physiological characteristics of the *Guzmania* hybrid 'TINTO'. The present invention also relates to methods for producing these seeds and plants of the *Guzmania* hybrid 'TINTO'. Furthermore, the present invention relates to a method of producing progeny *Guzmania* plants by crossing *Guzmania* 'TINTO', as either the female or seed or male or pollen parent, with another *Guzmania* plant and selecting progeny.

BACKGROUND OF THE INVENTION

The present invention relates to a new, distinct and stable hybrid of *Guzmania* hybrid, hereinafter referred to by the variety denomination 'TINTO'. The new *Guzmania* 'TINTO' originated from a cross made in a controlled breeding program by the inventors in 2002, and then first flowered in 2005, in Assendelft, The Netherlands. The female or seed parent is the *Guzmania lingulata* minor inbred line identified by code 02270322 (unpatented). The male or pollen parent is the *Guzmania lingulata* inbred line identified by code 02270835 (unpatented).

*Guzmania* is a member of the Bromeliaceae family. *Guzmania* is predominantly epiphytic with a few terrestrial species and is native to the tropics. For the most part, species vary in diameter from 7 or 8 inches to 3 or 4 feet and have rosettes of TINTO, smooth-edged leaves.

Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived.

*Guzmania* may be advantageously grown as pot plants for greenhouse or home use. Typically, the plants are shaded from direct sunlight. During the spring to autumn period, the central vase-like part of the leaf rosette is normally filled with water.

*Guzmania* is native to tropical America. Leaves of *Guzmania* are usually formed as basal rosettes which are stiff and entire and in several vertical ranks. *Guzmania* plants have terminal spikes or panicles which are often bracted with petals united in a tube about as long as the calyx. The ovary is superior and the seeds plumose.

Asexual propagation of *Guzmania* is frequently performed by vegetative means through the use of tissue culture practices. Propagation of *Guzmania* can also be from offshoots which can be detached from the mother plant and grown in an appropriate soil or bark mixture.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

A *Guzmania* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect their morphological and physiological characteristics.

A need exists for a greater variety of *Guzmania* cultivars with attractive ornamental features. Additionally, a need exists for additional *Guzmania* hybrid cultivars that can be easily propagated by seed. The new *Guzmania* 'TINTO' was developed through a controlled breeding program and exhibits unique, desirable and stable characteristics.

SUMMARY OF THE INVENTION

The present invention provides *Guzmania* plant selections that are solid, medium-sized, long-lasting hybrids with superior bract production and a singular wine red inflorescence that exhibits good keeping quality. The present invention also provides *Guzmania* plant selections with a round, spike-like inflorescence with a unique wine red color which distinguishes the new cultivar from typical *Guzmania*.

These and other objectives have been achieved in accordance with the present invention which provides 'TINTO' as a new *Guzmania* cultivar that is a product of a planned breeding program conducted by the inventors, Elly Bak and Nico D. M. Steur, in Assendelft, The Netherlands, in 2000. The female or seed parent is the *Guzmania lingulata* minor inbred line identified by code 02270322 (unpatented). The male or pollen parent is the *Guzmania lingulata* inbred line identified by code 02270835 (unpatented).

Both parental cultivars have a sufficient degree of homozygosity such that the progeny of the cross are genetypically and phenotypically uniform. The new hybrid 'TINTO' therefore can be produced by sexual reproduction by crossing the parental inbred lines identified by the codes 02270322 and 02270835 to produce a population of progeny plants, each of which has the combination of characteristics as herein disclosed for the new hybrid 'TINTO'.

Seeds which are the hybrid 'TINTO' are produced by crossing the parental inbred lines identified by the codes 02270322 and 02270835, and are deposited with the American Type Culture Collection, 10801 University Boulevard, Manassas, Va. 20110-2209. ATCC Patent Deposit Designation No. PTA-8834. 2500 seeds were deposited with the ATCC on Dec. 3, 2007.

OBJECTS OF THE INVENTION

The present invention relates to seeds which produce *Guzmania* hybrid 'TINTO'. The present invention also relates to *Guzmania* plants, and parts thereof, having all the physiological and morphological characteristics of *Guzmania* hybrid 'TINTO'. The present invention relates to a plant produced from seeds which are *Guzmania* hybrid 'TINTO'. The present invention also relates to plant parts, such as pollen, seeds or inflorescence produced by *Guzmania* hybrid 'TINTO'.

The present invention relates to a method of producing seed which are *Guzmania* hybrid 'TINTO', by crossing *Guzmania lingulata* minor inbred line identified by code 02270322 (unpatented) as the female or seed parent with *Guzmania lingulata* inbred line identified by code 02270835 (unpatented) as the male or pollen parent, and the reciprocate cross with 02270835 as the female parent and 02270322 as the male parent, and harvesting seeds produced from said crosses.

The present invention also relates to a method of producing plants having all the physiological and morphological characteristics of the *Guzmania* hybrid 'TINTO' comprising the steps of (a) crossing *Guzmania lingulata* minor inbred line identified by code 02270322 (unpatented) as the female or seed parent with *Guzmania lingulata* inbred line identified by code 02270835 (unpatented) as the male or pollen parent; (b) harvesting seeds produced from said cross; and (c) producing plants from said harvested seeds.

The present invention also relates to producing progeny plants from the cross of *Guzmania* hybrid 'TINTO', as the female or male parent, with another *Guzmania* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Guzmania* hybrid 'TINTO' showing the colors as true as is reasonably possible with colored reproductions of this type. Colors in the photographs may differ slightly from the color values cited in the detailed botanical description which accurately describes the color of 'TINTO'.

DETAILED BOTANICAL DESCRIPTION

Figure 1:
FIG. 1 shows a side view perspective of the primary and top bracts produced by a typical potted, flowering plant of 'TINTO', at 11 months of age from potting size.
Figure 2:
FIG. 2 shows a close-up top view perspective of the inflorescence and top bracts produced by a typical potted, flowering plant of 'TINTO', at 11 months of age from potting size.

The present invention was created by the inventors, Elly Bak and Nicolaas D. M. Steur in 2002, and flowered for the first time in 2005 in Assendelft, The Netherlands.

This invention is directed to *Guzmania* plant having all the morphological and physiological characteristics of the hybrid 'TINTO' produced from seeds which are the product of the cross of the *Guzmania lingulata* minor inbred line identified by code 02270322 (unpatented) as the female or seed parent with the *Guzmania lingulata* inbred line identified by code 02270835 (unpatented) as the male or pollen parent. Both parents have a sufficient degree of homozygosity such that the progeny of the cross were, and continue to be, phenotypically uniform. The new hybrid 'TINTO' can therefore be produced by sexual reproduction by crossing of the inbred selections identified by the codes 02270322 and 02270835 to produce a population of progeny plants, each of which has the combination of characteristics herein disclosed for the new hybrid 'TINTO'.

The new hybrid 'TINTO' can also be produced by asexually reproducing progeny from the cross of the parental inbred lines identified by the codes 02270322 and 02270835. Asexual reproduction of the new cultivar by vegetative means by cuttings was first performed in 2005, in Assendelft, The Netherlands. The first 'TINTO' plants propagated through the use of such cuttings flowered in 2007, in Assendelft, The Netherlands, and have demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'TINTO' which in combination distinguish this *Guzmania* as a new and distinct cultivar:

1. Solid growth habit;
2. Funnel-form rosette plant, measuring about 21 cm in height (above the pot when flowering);
3. Numerous, relatively narrow, green color foliage, measuring about 23 cm in length and about 2.0 cm to 3.5 cm in width;
4. Superior floral bract production;
5. Bracts have a unique wine red color which distinguishes this cultivar from typical *Guzmania*;
6. Round, singular inflorescence, measuring about 6 cm in height and about 13 cm in diameter; and
7. Long-lasting habit.

Plants of the parental lines, 02270322 and 02270835 (both unpatented) are no longer available to provide a detailed botanical comparison with the new *Guzmania* hybrid 'TINTO'

Of the many commercial cultivars known to the present inventors, the most similar in comparison to the new *Guzmania* hybrid 'TINTO' is the *Guzmania* cultivar 'TEMPO' (granted, U.S. Pat. No. 6,403,868). Plants of the new hybrid 'TINTO' differ from plants of 'TEMPO' primarily in inflorescence color. Plants of 'TINTO' produce inflorescence which are wine red (closest to RHS 53A of the Red Group) whereas plants of 'TEMPO' produce inflorescence which are red (closest to RHS 44A of the Red Group).

'TINTO' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, can result depending on the size of the plant at the time that flowering is induced by acetylene treatment. Since treatment with acetylene to induce flowering disrupts normal watering and fertilization regimens, acetylene treatment of relatively smaller plants adversely affects the growth of the plant.

The aforementioned photographs, together with the following observations, measurements and values describe the new *Guzmania* 'TINTO' as grown in a greenhouse in Assendelft, The Netherlands, under conditions which closely approximate those generally used in commercial practice. Plants of 'TINTO' were grown in a greenhouse with day temperatures ranging from 20° C. to 28° C. and night temperatures ranging from 18° C. to 23° C. No artificial lighting or photoperiodic treatments were conducted, but plants of 'TINTO' are forced into flowering by adding acetylene. The following fertilizer is added when growing plants of 'TINTO': 1 part nitrogen, 0.6 parts phosphor, 2 parts Kalium and 0.1 parts magnesium.

Color references are made to the Royal Horticultural Society Colour Chart (RHS), 2001 edition, except where general colors of ordinary significance are used. Color values were taken under daylight conditions in a greenhouse in Assendelft, The Netherlands. The age of the plants of 'TINTO' described is about 11 weeks after treatment with acetylene.

Classification:
Botanical: *Guzmania* sp.

Parentage:
Female Parent: *Guzmania lingulata* minor inbred line identified by code 02270322 (unpatented)
Male Parent: *Guzmania lingulata* inbred line identified by code 02270835 (unpatented)

Plant:
  General Appearance and Form:
    Height: About 21 cm (when flowering)
    Width: About 42 cm
    Shape: Funnel form rosette
  Growth habit: Stemless
  Plant Vigor: Good
  Flowering Season: A fully grown plant can flower year round, starting 11 weeks after induction of natural light or trough treatment with acetylene.
  Cold Tolerance: Frost tender. Temperatures below 5° C. may damage plants.
  Fragrance: None Foliage:
Quantity: About 25 (depending on the size of the plant)
Size of Leaf:
  Length: About 23 cm (when flowering)
  Width: About 2.0 cm to 3.5 cm
Overall Shape: Linear-lanceolate
Apex Shape: Acute
Base Shape: Strap-like around central axis
Margin: Entire
Texture: Smooth
Orientation: Leaf blades arch continuously from base.
Color: Leaf color can vary somewhat depending on growing conditions
  Upper Surface: Green, RHS 137C with yellow-green, RHS 146A
  Lower Surface: Yellow-green, RHS 146A
  Venation: None Inflorescence:
Borne: Erect stalks
Shape: Round, singular head
Size:
  Length: About 6 cm
  Diameter: About 13 cm
Time of Bloom: A fully grown plant can produce an inflorescence containing about 25 flowers (depending on the size of the plants), and can bloom the whole year starting about eleven (11) weeks after natural induction or through treatment with acetylene.
Duration of Bloom: Each flower blooms one (1) day and the total blooming of the whole inflorescence is about six (6) weeks.
Petals:
  Number: 3 per flower
  Length: About 5.5 cm
  Width: About 0.5 cm
  Overall Shape: Ligulate
  Apex Shape: Obtuse
  Base Shape: Fused
  Color:
    Upper surface: Yellow-orange, RHS 15A, with white tip
    Lower surface: Yellow-orange, RHS 15A, with white tip
Sepals:
  Number: 3 per flower
  Length: About 2.5 cm
  Width: About 0.3 cm
  Overall Shape: Ligulate
  Apex Shape: Acute
  Base Shape: Fused
  Color: Translucent
Bracts:
Scape Bracts:
  Quantity: About 6
  Arrangement: Alternate
  Size:
    Length: About 15 cm (lowest) to about 9 cm (scape bracts positioned just below the primary bracts).
    Width: About 3.0 cm
  Overall shape: Lanceolate
  Apex shape: Acute
  Base shape: Fused
  Margin: Entire
  Texture: Smooth
  Color:
    Upper and under surfaces: Lowest bracts are mostly green, closest to RHS 137C, with a wine red color, closest to RHS 53A, and then changing to mostly wine red, closest to RHS 185A, with a little yellow-green, closest to RHS 185A, just below primary bracts.
Primary Bracts:
  Quantity: About 14
  Arrangement: Alternate
  Size:
    Length: About 10 cm (lowest) to about 5 cm (primary bracts become shorter closer to the top of plant)
    Width: About 3.0 cm
  Overall shape: Recurved and ovate-lanceolate
  Apex shape: Acute
  Base shape: Fused
  Margin: Entire
  Texture: Smooth
  Color:
    Upper and lower surfaces: Red, closest to RHS 39A, with greyed-purple, RHS 185A, with yellow-orange, RHS 15A, tip
Floral bracts: Disposed within the inflorescence.

Reproductive Organs:
Androecium:
  Stamen:
    Number: 6 per flower
    Length: About 5 cm
    Diameter: Less than 1 mm
    Color: White
  Anther:
    Length: About 0.5 cm
    Color: White
  Pollen:
    Amount: Scarce
    Color: White
Gynoecium:
  Pistil:
    Number: 1 per flower
    Length: About 4.5 cm
  Stigma:
    Shape: 3-parted
    Width: About 1 mm
    Color: Yellow, RHS 2D
  Style:
    Length: About 4.4 cm
    Color: Yellow, RHS 2D Ovary:
    Position: Superior
    Shape: Conical
    Length: About 0.6 cm
    Diameter: About 0.3 cm
    Color: Yellow, RHS 2D Seeds:
    Quantity: About 5000 seeds are provided, divided among 25 capsules (depending on the size of the plant). Since the new cultivar is a hybrid, the seeds produced by the plant can not be used for reproduction.
    Size:
        Length: About 4 cm
        Diameter: Less than 1 mm
    Color: Brown (too small to qualify RHS designation)
    Texture: Plumose Fruit:
    Quantity: About 25 (depending on size of plant)
    Type: Capsule
    Size:
        Length: About 3 cm
        Diameter: About 0.6 cm
    Color: Greyed-orange, closest to RHS 165A and RHS 165B
    Texture: Smooth Disease/Pest Resistance: No observations made.

Disease/Pest Susceptibility: No observations made.

We claim:

1. A *Guzmania* plant named 'TINTO', representative seed having been deposited with the American Type Culture Collection (ATCC) and accorded Patent Deposit Designation No.: PTA-8834.

2. A *Guzmania* seed having American Type Culture Collection (ATCC) Patent Deposit Designation No.: PTA-8834.

3. A plant part obtained from the *Guzmania* plant of claim 1.

4. A method of producing *Guzmania* progeny plant comprising the steps of (a) crossing *Guzmania* 'TINTO ' representative seed having been deposited with the American Type Culture Collection (ATCC) and accorded Patent Deposit Designation No.: PTA-8834 as a female or male parent with another *Guzmania* plant, and (b) selecting progeny.

5. A method according to claim 4, wherein the second *Guzmania* plant is 'TINTO'.

* * * * *